(12) United States Patent
Tsujioka et al.

(10) Patent No.: US 6,485,868 B1
(45) Date of Patent: *Nov. 26, 2002

(54) ELECTROLYTE FOR ELECTROCHEMICAL DEVICE

(75) Inventors: Shoichi Tsujioka, Saitama (JP); Hironari Takase, Saitama (JP); Mikihiro Takahashi, Saitama (JP)

(73) Assignee: Central Glass Company, Limited, Ube (JP)

( * ) Notice: Subject to any disclaimer, the term of this patent is extended or adjusted under 35 U.S.C. 154(b) by 12 days.

This patent is subject to a terminal disclaimer.

(21) Appl. No.: 09/625,353

(22) Filed: Jul. 25, 2000

(30) Foreign Application Priority Data

Aug. 2, 1999 (JP) .............................. 11-219044
Mar. 13, 2000 (JP) ........................... 2000-069202

(51) Int. Cl.$^7$ ................................. H01M 6/18
(52) U.S. Cl. .................. 429/306; 429/322; 252/62.2; 544/54
(58) Field of Search .................. 429/306, 322; 252/62.2; 544/54

(56) References Cited

FOREIGN PATENT DOCUMENTS

JP    2000-173343 A2 *  6/2000

OTHER PUBLICATIONS

Redshaw et al. "Interaction of cyclohexyl isocyanate with oxoruthenium (V) 2–alkyl–2–hydroxybutyrates" J. Chem. Soc., Dalton Trans. (1992), (13), 2059–2062.*

* cited by examiner

Primary Examiner—Laura Weiner
(74) Attorney, Agent, or Firm—Crowell & Moring LLP

(57) ABSTRACT

The invention relates to an electrolyte for an electrochemical device. This electrolyte includes an ionic metal complex represented by the general formula (1):

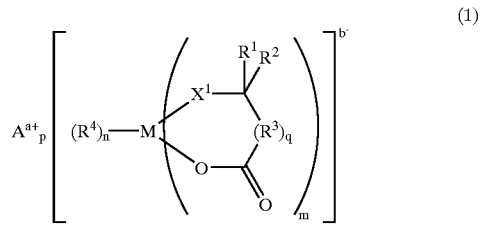

wherein M is an element of groups 3–15 of the periodic table; $A^{a+}$ represents a metal ion, onium ion or proton; $X^1$ represents O, S or $NR^5R^6$; each of $R^1$ and $R^2$ independently represents H, a halogen, a $C_1$–$C_{10}$ alkyl group or $C_1$–$C_{10}$ halogenated alkyl group; $R^3$ represents a $C_1$–$C_{10}$ alkylene group, $C_1$–$C_{10}$ halogenated alkylene group, $C_4$–$C_{20}$ aryl group or $C_4$–$C_{20}$ halogenated aryl group; $R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$; $X^2$ represents O, S or $NR^5R^6$; each of $R^5$ and $R^6$ represents H or a $C_1$–$C_{10}$ alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group. The electrolyte has high heat resistance and hydrolysis resistance as compared with conventional electrolytes.

16 Claims, No Drawings

ELECTROLYTE FOR ELECTROCHEMICAL DEVICE

BACKGROUND OF THE INVENTION

The present invention relates to an electrolyte including an ionic metal complex having a novel chemical structure, an ionic conductor including the electrolyte, and electrochemical devices including the electrolyte, such as lithium cells, lithium ion cells, electrical double-layer capacitors.

Accompanying the evolution of portable equipment in recent years, there has been active development of electrochemical devices utilizing electrochemical phenomena, such as cells for use as their power supplies and capacitors. In addition, electrochromic devices (ECD), in which a color change occurs due to an electrochemical reaction, are examples of electrochemical devices for uses other than power supplies.

These electrochemical devices are typically composed of a pair of electrodes and an ionic conductor filled between them. The ionic conductor contains a salt (AB) as an electrolyte, which is dissolved in a solvent, polymer or mixture thereof such that the salt is dissociated into cations ($A^+$) and anions ($B^-$), resulting in ionic conduction. In order to obtain the required level of ion conductivity for the device, it is necessary to dissolve a sufficient amount of this electrolyte in solvent or polymer. In actuality, there are many cases in which a solvent other than water is used, such as organic solvents and polymers. Electrolytes having sufficient solubility in such organic solvents and polymers are presently limited to only a few types. For example, electrolytes having sufficient solubility for use in lithium cells are only $LiClO_4$, $LiPF_6$, $LiBF_4$, $LiAsF_6$, $LiN(CF_3SO)_2$ and $LiCF_3SO_3$. Although the cation type of the electrolyte is frequently limited by the device as is the case with the lithium ion of lithium cells, any anion can be used for the electrolyte provided it satisfies the condition of having high solubility.

Amidst the considerable diversity of the application range of these devices, efforts are made to seek out the optimum electrolyte for each application. Under the present circumstances, however, optimization efforts have reached their limit due to the limited types of available anions. In addition, existing electrolytes have various problems, thereby creating the need for an electrolyte having a novel anion portion. More specifically, since $ClO_4$ ion of $LiClO_4$ is explosive and $AsF_6$ ion of $LiAsF_6$ is toxic, they cannot be used for reasons of safety. Since $LiN(CF_3SO_2)_2$ and $LiCF_3SO_3$ corrode the aluminum collector inside the cell when a potential is applied, their use presents difficulties. Even the only practical electrolyte of $LiPF_6$ ends up decomposing at temperatures of 70° C. and above, having problems including heat resistance and hydrolysis resistance.

SUMMARY OF THE INVENTION

It is therefore an object of the present invention to provide a useful novel electrolyte, a novel ion conductor containing the electrolyte, and a novel electrochemical device containing the ion conductor.

According to the present invention, there is provided an electrolyte for an electrochemical device. This electrolyte comprises an ionic metal complex represented by the general formula (1):

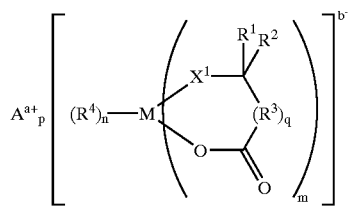

wherein M is a transition metal selected from the group consisting of elements of groups 3–11 of the periodic table, or an element selected from the group consisting of elements of groups 12–15 of the periodic table; $A^{a+}$ represents a metal ion, onium ion or proton; a represents a number from 1 to 3; b represents a number from 1 to 3; p is b/a; m represents a number from 1 to 3; n represents a number from 0 to 4; q is 0 or 1; $X^1$ represents O, S or $NR^5R^6$; each of $R^1$ and $R^2$ independently represents H, a halogen, a $C_1$–$C_{10}$ alkyl group or $C_1$–$C_{10}$ halogenated alkyl group; $R^3$ represents a $C_1$–$C_{10}$ alkylene group, $C_1$–$C_{10}$ halogenated alkylene group, $C_4$–$C_{20}$ aryl group or $C_4$–$C_{20}$ halogenated aryl group; $R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$; $X^2$ represents O, S or $NR^5R^6$; each of $R^5$ and $R^6$ represents H or a $C_1$–$C_{10}$ alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group.

According to the present invention, there is provided an ion conductor for an electrochemical device. This ion conductor comprises the electrolyte; and a member selected from the group consisting of a nonaqueous solvent, a polymer and a mixture thereof, said member dissolving therein said electrolyte.

According to the present invention, there is provided an electrochemical device comprising (a) first and second electrodes; and (b) the ion conductor receiving therein said first and second electrodes.

An electrolyte according to the present invention has high heat resistance and hydrolysis resistance as compared with conventional electrolytes. Thus, the electrolyte can advantageously be used for electrochemical devices such as lithium cell, lithium ion cell and electrical double-layer capacitor.

DESCRIPTION OF THE PREFERRED EMBODIMENTS

According to the invention, the alkyl groups, halogenated alkyl groups, aryl groups and halogenated aryl groups, which are contained in the ionic metal complex and the raw materials for synthesizing the same, may be branched and/or may have other functional groups such as hydroxyl groups and ether bonds.

The followings are specific nine examples of the ionic metal complex represented by the general formula (1) of the present invention.

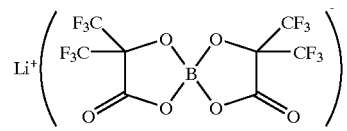

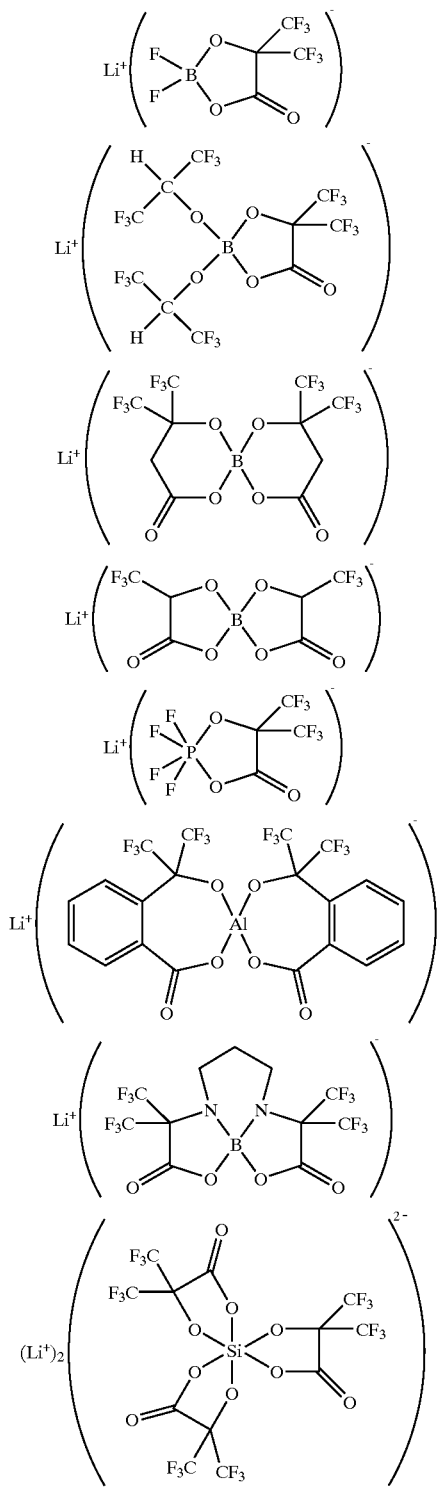

Here, although lithium ion is indicated as an example of $A^{a+}$ of the general formula (1), examples of other cations that can be used other than lithium ion include sodium ion, potassium ion, magnesium ion, calcium ion, barium ion, cesium ion, silver ion, zinc ion, copper ion, cobalt ion, iron ion, nickel ion, manganese ion, titanium ion, lead ion, chromium ion, vanadium ion, ruthenium ion, yttrium ion, lanthanoid ion, actinoid ion, tetrabutylammonium ion, tetraethylammonium ion, tetramethylammonium ion, triethylmethylammonium ion, triethylammonium ion, pyridinium ion, imidazolium ion, proton, tetraethylphosphonium ion, tetramethylphosphonium ion, tetraphenylphosphonium ion, triphenylsulfonium ion, and triethylsulfonium ion. In the case of considering the application of the ionic metal complex for electrochemical devices and the like, lithium ion, tetraalkylammonium ion and proton are preferable. As shown in the general formula (1), the valency (valence) of the $A^{a+}$ cation is preferably from 1 to 3. If the valency is larger than 3, the problem occurs in which it becomes difficult to dissolve the ionic metal complex in solvent due to the increase in crystal lattice energy. Consequently, in the case of requiring solubility of the ionic metal complex, a valency of 1 is preferable. As shown in the general formula (1), the valency (b−) of the anion is similarly preferably from 1 to 3, and a valency of 1 is particularly preferable. The constant p expresses the ratio of the valency of the anion to the valency of the cation, namely b/a.

In the general formula (1), M at the center of the ionic metal complex of the present invention is selected from elements of groups 3–15 of the periodic table. It is preferably Al, B, V, Ti, Si, Zr, Ge, Sn, Cu, Y, Zn, Ga, Nb, Ta, Bi, P, As, Sc, Hf or Sb, and more preferably Al, B or P. Although it is possible to use various elements for the M other than these preferable examples, synthesis is relatively easy in the case of using Al, B, V, Ti, Si, Zr, Ge, Sn, Cu, Y, Zn, Ga, Nb, Ta, Bi, P, As, Sc, Hf or Sb. In addition to ease of synthesis, the ionic metal complex has excellent properties in terms of low toxicity, stability and production cost in the case of using Al, B or P.

In the general formula (1), the organic or inorganic portion bonded to M is referred to as the ligand. As mentioned above, $X^1$ in the general formula (1) represents O, S or $NR^5R^6$, and is bonded to M through its hetero atom (O, S or N). Although the bonding of an atom other than O, S or N is not impossible, the synthesis becomes extremely bothersome. The ionic metal complex represented by the general formula (1) is characterized by these ligands forming a chelate structure with M since there is bonding with M by a carboxyl group (—COO—) other than $X^1$ within the same ligand. As a result of this chlelation, the heat resistance, chemical stability and hydrolysis resistance of the ionic metal complex are improved. Although constant q in this ligand is either 0 or 1, in the case of 0 in particular, since the chelate ring becomes a five-member ring, chelating effects are demonstrated most prominently, making this preferable due to the resulting increase in stability. In addition, since the negative charge of the central M is dissipated by electron attracting effects of the carboxyl group(s) resulting in an increase in electrical stability of the anion, ion dissociation becomes extremely easy resulting in corresponding increases of the ionic metal complex in solvent solubility, ion conductivity, catalyst activity and so forth. In addition, the other properties of heat resistance, chemical stability and hydrolysis resistance are also improved.

In the general formula (1), each of $R^1$ and $R^2$ is independently selected from H, halogen, $C_1$–$C_{10}$ alkyl groups and $C_1$–$C_{10}$ halogenated alkyl groups. At least one of either $R^1$ and $R^2$ is preferably a fluorinated alkyl group, and more preferably, at least one of $R^1$ and $R^2$ is a trifluoromethyl group. Due to the presence of an electron-attracting halogen and/or a halogenated alkyl group for $R^1$ and $R^2$, the negative charge of the central M is dissipated. This results in an increase of the anion of the general formula (1) in electrical stability. With this, the ion dissociation becomes extremely easy resulting in an increase of the ionic metal complex in solvent solubility, ion conductivity, catalyst activity and so forth. In addition, other properties of heat resistance, chemical stability and hydrolysis resistance are also improved. The case in which the halogen is fluorine in particular has significant advantageous effects, while the case of a trifluoromethyl group has the greatest advantageous effect.

In the general formula (1), $R^3$ is selected from $C_1$–$C_{10}$ alkylene groups, $C_1$–$C_{10}$ halogenated alkylene groups, $C_4$–$C_{20}$ aryl groups and $C_4$–$C_{20}$ halogenated aryl groups. $R^3$ is preferably one which forms a 5 to 10-membered ring when a chelate ring is formed with the central M. The case of a ring having more than 10 members is not preferable, since chelating advantageous effects are reduced. In addition, in the case $R^3$ has a portion of hydroxyl group or carboxyl group, it is possible to form a bond between the central M and this portion.

In the general formula (1), $R^4$ is selected from halogens, $C_1$–$C_{10}$ alkyl groups, $C_1$–$C_{10}$ halogenated alkyl groups, $C_4$–$C_{20}$ aryl groups, $C_4$–$C_{20}$ halogenated aryl groups and $X^2R^7$. Of these, fluorine is preferable. $X^2$ represents O, S or $NR^5R^6$ and bonds to M through one of these heteroatoms (O, S and N). Although the bonding of an atom other than O, S or N is not impossible, the synthesis becomes extremely bothersome. Each of $R^5$ and $R^6$ is selected from H and $C_1$–$C_{10}$ alkyl groups. Each of $R^5$ and $R^6$ differs from other groups (e.g., $R^1$ and $R^2$) in that the former is not required to be an electron attracting group. In the case of introducing an electron attracting group as $R^5$ or $R^6$, the electron density on N of $NR^5R^6$ decreases, thereby preventing coordination on the central M. $R^7$ is selected from $C_1$–$C_{10}$ alkyl groups, $C_1$–$C_{10}$ halogenated alkyl groups, $C_4$–$C_{20}$ aryl groups and $C_4$–$C_{20}$ halogenated aryl groups. Of these, a $C_1$–$C_{10}$ fluorinated alkyl groups is preferable. Due to the presence of an electron-attracting halogenated alkyl group as $R^7$, the negative charge of the central M is dissipated. Since this increases the electrical stability of the anion of the general formula (1), ion dissociation becomes extremely easy resulting in an increase of the ionic metal complex in solvent solubility, ion conductivity and catalyst activity. In addition, other properties of heat resistance, chemical stability and hydrolysis resistance are also improved. The case in which the halogenated alkyl group as $R^7$ is a fluorinated alkyl group in particular results in even greater advantageous effects.

In the general formula (1), the values of the constants m and n relating to the number of the above-mentioned ligands depend on the type of the central M. In fact, m is preferably from 1 to 3, while n is preferably from 0 to 4.

The anion of the ionic metal complex represented by the general formula (1) is stabilized by having therein a halogenated alkyl group with strong electron attraction, and particularly a trifluoromethyl group ($CF_3$ group) and carbonyl group (C=O group), thereby facilitating dissociation of the ionic metal complex into the anion and cation. This is extremely important in the case of using as the electrolyte of an electrochemical device. Although there are an almost infinite number of salts referred to as electrolytes, the majority dissolve and dissociate in water, and thereby are ion conductive. Many of such salts do not even dissolve in organic solvents and so forth other than water. Such aqueous solutions are used as an electrolytic solution of electrochemical devices. However, due to the low decomposition potential of water as a solvent and its susceptibility to oxidation and reduction, there are many restrictions on its use. For example, in a lithium cell and so forth, since the potential difference between the electrodes of the device is 3 V or more, water ends up being electrolyzed into hydrogen and oxygen. There are many organic solvents and polymers that are insusceptible to oxidation and reduction as compared with water due to their structures. Therefore, they are used in devices requiring higher voltages such as lithium cells and electrical double-layer capacitors.

In comparison with conventional electrolytes, the electrolyte of the present invention is extremely soluble in organic solvent and dissociates more easily due to the above-mentioned effects of $CF_3$ groups and C=O groups and a large size of the anion of the ionic metal complex. Consequently, an electrolytic solution containing an electrolyte of the ionic metal complex dissolved in an organic solvent can be used as a superior ion conductor of electrochemical devices such as lithium cells. Complexes of organic substances and metals are typically susceptible to hydrolysis and there are many that are chemically unstable. Since the electrolyte of the present invention, however, has a chelate structure, it is extremely stable and resistant to hydrolysis and so forth. In addition, that having fluorine within the chemical structure represented by the general formula (1) is particularly preferable since it further increases chemical stability such as oxidation resistance due to the effect of the fluorine.

Optimization of the chemical structure of the general formula (1) makes it possible to obtain an electrolyte that dissolves in organic solvents in which conventional electrolytes do not dissolve, examples of which include toluene, hexane and fluorine-containing organic solvents such as fluorohydrocarbons.

Although the electrolyte of the present invention is used as the electrolyte of electrochemical devices such as lithium cells (cells), lithium ion cells (cells) and electrical double-layer capacitors, examples of its other applications include catalysts of organic synthesis reactions, polymerization catalysts and co-catalysts (auxiliary catalysts) of olefin polymerization.

There are no particular restrictions on the process for synthesizing the electrolyte of the present invention. For example, an ionic metal complex (electrolyte) having the following formula can be synthesized by reacting LiB $(OCH_3)_4$ with a stoichiometric amount of $HOC(CF_3)_2COOH$.

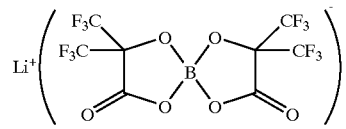

In the case of preparing an electrochemical device using an electrolyte of the present invention, its basic structural elements are ion conductor, negative electrode, positive electrode, collector, separator, container and the like.

A mixture of electrolyte and non-aqueous solvent or polymer is used as the ion conductor. If a non-aqueous solvent is used, the resulting ion conductor is typically referred to as an electrolytic solution, while if a polymer is used, it is typically referred to as a polymer solid electrolyte. Non-aqueous solvent may also be contained as plasticizer in polymer solid electrolytes. It is possible to use one type or a mixture of two or more types of an electrolyte of the present invention. In the case of mixing, it is necessary that one type be an electrolyte of the present invention, while examples of other electrolytes that can be used include lithium salts such as $LiClO_4$, $LiPF_6$, $LiBF_4$, $LiCF_3SO_3$, $LiN(CF_3SO_2)_2$ and $LiSbF_6$.

There are no particular restrictions on the non-aqueous solvent provided it is an aprotic solvent that is able to dissolve an electrolyte of the present invention, and examples of this non-aqueous solvent that can be used include carbonates, esters, ethers, lactones, nitrites, amides and sulfones. In addition, the solvent can either be used alone or in the form of a mixture of two or more types of solvent. Specific examples of the solvent include propylene carbonate, ethylene carbonate, diethyl carbonate, dimethyl carbonate, methylethyl carbonate, dimethoxyethane, acetonitrile, propionitrile, tetrahydrofuran, 2-methyltetrahydrofuran, dioxane, nitromethane, N,N-dimethylformamide, dimethylsulfoxide, sulfolane and γ-butyrolactone.

There are no particular restrictions on the polymer to be mixed with the electrolyte of the invention provided it is an aprotic polymer that can dissolve the electrolyte. Examples of such polymer include polymers having polyethylene oxide on their main chain or side chain, homopolymers or copolymers of polyvinylidene fluoride, methacrylate polymers and polyacrylonitrile. In the case of adding plasticizer to these polymers, the above-mentioned aprotic non-aqueous solvent can be used. The concentration of the electrolyte of the present invention in these ion conductors is preferably 0.1 mol/dm$^3$ or more up to the saturated concentration, and more preferably from 0.5 mol/dm$^3$ to 1.5 mol/dm$^3$. If the concentration is lower than 0.1 mol/dm$^3$, ion conductivity may become too low.

There are no particular restrictions on the negative electrode material for preparing an electrochemical device. In the case of lithium cell, lithium metal (metallic lithium) or an alloy of lithium and another metal can be used. In the case of a lithium ion cell, it is possible to use an intercalation compound containing lithium atoms in a matrix of another material, such as carbon, natural graphite or metal oxide. This carbon can be obtained by baking polymer, organic substance, pitch or the like. In the case of electrical double-layer capacitor, it is possible to use activated carbon, porous metal oxide, porous metal, conductive polymer and so forth.

There are no particular restrictions on the positive electrode material. In the case of lithium cell or lithium ion cell, lithium-containing oxides such as $LiCoO_2$, $LiNiO_2$, $LiMnO_2$ and $LiMn_2O_4$; oxides such as $TiO_2$, $V_2O_5$ and $MoO_3$; sulfides such as $TiS_2$ and FeS; and electrically conductive polymers such as polyacetylene, polyparaphenylene, polyaniline or polypyrrole can be used. In the case of electrical double-layer capacitor, activated carbon, porous metal oxide, porous metal, electrically conductive polymer and so forth can be used.

The following nonlimitative examples are illustrative of the present invention.

EXAMPLE 1

In a glove box having an atmosphere of a dew point of −50° C., 20.2 g of hexafluoro-2-hydroxyisobutyric acid (HOC(CF$_3$)$_2$COOH) were dissolved in 20 ml of dimethyl carbonate. Next, 6.8 g of lithium tetrakis(methoxy)borate (LiB(OCH$_3$)$_4$) were slowly added to this solution. After this addition, the solution was heated to 60° C. and allowed to react for 3 hours. Dimethyl carbonate was removed from the resulting reaction solution under a reduced pressure condition of 170° C. and 1 torr, thereby obtaining 20.0 g of a white solid as a product. This product was identified by NMR spectrum and elementary analysis as being LiB(OC(CF$_3$)$_2$COO)$_2$ having the following formula.

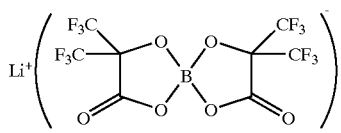

The NMR spectrum of the product is shown below.
$^{19}$F-NMR (hexafluorobenzene standard, solvent: CD$_3$CN) 88.1 ppm (6F, q, J=8 Hz) 88.3 ppm (6F, q, J=8 Hz)
$^{11}$B-NMR (B(OCH$_3$)$_3$ standard, solvent: CD$_3$CN) −8.5 ppm (s)

Next, the obtained compound was dissolved in a mixed solution of ethylene carbonate (EC) and dimethyl carbonate (DMC) (EC:DMC=1:1) to prepare an electrolytic solution having an electrolyte concentration of 1 mol/dm$^3$ followed by measurement of ion conductivity with an alternating current bipolar-type cell. As a result, the ion conductivity was 7.0 mS/cm.

The above-mentioned electrolyte was placed in a container made of fluororesin. When stored for 1 month at 100° C. as a heat resistance test, there was no discoloration or other deterioration of the electrolytic solution. In addition, when water was added to this electrolytic solution, it was found by NMR that the electrolytic solution had not been subjected to hydrolysis at all.

A corrosion test of an aluminum collector was performed using the above-mentioned electrolytic solution. A beaker type cell was used for the test cell, using aluminum for the working electrode, and lithium metal (metallic lithium) for the counter electrode and reference electrode. When the working electrode was held at 5 V (Li/Li$^+$), there was no flow of current whatsoever. Following testing, although the surface of the working electrode w was observed by SEM, there were no changes observed in comparison with that before testing.

A charging and discharging test of an actual cell was performed using the above-mentioned electrolytic solution. The test cell was prepared in the manner described below. The positive electrode was prepared by mixing 5 parts by weight of polyvinylidene fluoride (PVDF) as a binder and 5 parts by weight of acetylene black as a conductor with 90 parts by weight of an LiCoO$_2$ powder followed by the addition of N,N-dimethylformamide to form a paste. This paste was applied to an aluminum foil and allowed to dry to obtain the test positive electrode. Lithium metal was used for the negative electrode. A glass fiber filter as a separator was impregnated with the electrolytic solution, thereby assembling the cell.

Next, a constant current charging and discharging test was conducted as described below. The current density was 0.35 mA/cm$^2$ for both charging and discharging, while charging was performed until 4.2 V and discharging until 3.0 V (vs. Li/Li$^+$). As a result, the initial discharge capacity was 125 mAh/g. Although charging and discharging were repeated 20 times, results were obtained in which the capacity of the 20$^{th}$ cycle was 88% of the initial capacity.

EXAMPLE 2

In a glove box having an atmosphere of a dew point of −50° C., 10.0 g of hexafluoro-2-hydroxyisobutyric acid (HOC(CF$_3$)$_2$COOH) were dissolved in 20 ml of dimethyl carbonate. Next, a lithium methoxide/methanol solution containing 3.6 g of lithium methoxide (LiOCH$_3$) was slowly added to this solution. The dimethyl carbonate and methanol were removed under a reduced pressure condition of 60° C. and 1 torr, thereby obtaining LiOC(CF$_3$)$_2$COOLi as a product. After dissolving this compound in acetonitrile, 4.4 g of LiBF$_4$ were added to this solution, followed by heating to 60° C. and allowing to react for 10 hours. After filtering the LiF precipitate that formed during the reaction, the dimethyl carbonate was removed under a reduced pressure condition of 80° C. and 1 torr, thereby obtaining 12.5 g of a white solid as a product. This product was identified by NMR spectrum and elementary analysis as being LiBF$_2$(OC(CF$_3$)$_2$COO) having the following formula.

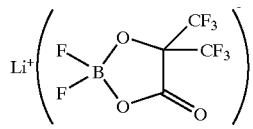

The NMR spectrum of the product is shown below.

$^{19}$F-NMR (hexafluorobenzene standard, solvent: CD$_3$CN) 15.3 ppm (2F, s) 88.2 ppm (6F, s)

$^{11}$B-NMR (B(OCH$_3$)$_3$ standard, solvent: CD$_3$CN) −14.1 ppm (t, J=4 Hz)

Next, the obtained compound was dissolved in a mixed solution of ethylene carbonate (EC) and dimethyl carbonate (DMC) (EC:DMC=1:1) to prepare an electrolytic solution having an electrolyte concentration of 1 mol/dm$^3$ followed by measurement of ion conductivity by the alternating current bipolar-type cell. As a result, the ion conductivity was 8.2 mS/cm.

A charging and discharging test of an actual cell was conducted using the above-mentioned electrolytic solution. The test cell (half cell) was prepared in the manner described below. 10 parts by weight of polyvinylidene fluoride (PVDF) as a binder were mixed with 90 parts by weight of natural graphite powder followed by the addition of N,N-dimethylformamide to prepare a slurry. This slurry was applied to a nickel mesh and allowed to dry for 12 hours at 150° C. to prepare a test negative electrode. Lithium metal was used for a counter electrode. A glass fiber filter as a separator was impregnated with the above-mentioned electrolytic solution, thereby assembling the half cell.

A constant current charging and discharging test was then conducted under the conditions indicated below. The current density was 0.3 mA/cm$^2$ for both charging and discharging, while charging was performed until 0.0 V and discharging until 1.5 V (vs. Li/Li$^+$). As a result, the initial discharge capacity was 320 mAh/g. Although charging and discharging were repeated 20 times, results were obtained in which the capacity of the 20$^{th}$ cycle was 95% of the initial capacity.

EXAMPLE 3

In a glove box having an atmosphere of a dew point of −50° C., 10.0 g of trifluorolactic acid (HOCH(CF$_3$)COOH) were dissolved in 20 ml of dimethyl carbonate. Next, 4.9 g of lithium tetrakis(methoxy)borate (LiB(OCH$_3$)$_4$) were slowly added to this solution. After this addition, the solution was heated to 60° C. and allowed to react for 3 hours. Dimethyl carbonate was removed from the resulting reaction solution under a reduced pressure condition of 170° C. and 1 torr, thereby obtaining 10.4 g of a white solid as a product. This product was identified by NMR spectrum and elementary analysis as being LiB(OCH(CF$_3$)COO)$_2$.

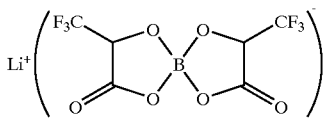

The NMR spectrum of the product is shown below.

$^{19}$F-NMR (hexafluorobenzene standard, solvent: CD$_3$CN) 87.12 ppm (3F, d, J=8 Hz) 87.18 ppm (3F, d, J=8 Hz) 87.32 ppm (3F, d, J=8 Hz)

Since the raw material, trifluorolactic acid, is a racemic modification having two types of optical isomers, three types of peaks were observed in $^{19}$F-NMR due to three combinations of (R,R), (S,S) and (R,S).

$^{1}$H-NMR 4.57 ppm (1H, q, J=8 Hz)

$^{11}$B-NMR (B(OCH$_3$)$_3$ standard, solvent: CD$_3$CN) −8.03 ppm (s)

Next, the obtained compound was dissolved in a mixed solution of ethylene carbonate (EC) and dimethyl carbonate (DMC) (EC:DMC=1:1) to prepare an electrolytic solution having an electrolyte concentration of 1 mol/dm$^3$ followed by measurement of ion conductivity by the alternating current bipolar-type cell. As a result, the ion conductivity was 6.3 mS/cm.

A charging and discharging test of an actual cell was conducted using the above-mentioned electrolyte. A test cell (half cell) was prepared in the manner described below. 10 parts by weight of polyvinylidene fluoride (PVDF) as a binder were mixed with 90 parts by weight of natural graphite powder followed by the addition of N,N-dimethylformamide to prepare a slurry. This slurry was applied to a nickel mesh and allowed to dry for 12 hours at 150° C. to prepare a test negative electrode. Lithium metal was used for a counter electrode. A glass fiber filter as a separator was impregnated with the above-mentioned electrolytic solution, thereby assembling the half cell.

A constant current charging and discharging test was then conducted under the conditions indicated below. The current density was 0.3 mA/cm$^2$ for both charging and discharging, while charging was performed until 0.0 V and discharging until 1.5 V (vs. Li/Li$^+$). As a result, the initial discharge capacity was 340 mAh/g. Although charging and discharging were repeated 20 times, results were obtained in which the capacity of the 20$^{th}$ cycle was 94% of the initial capacity.

EXAMPLE 4

In a glove box having an atmosphere of a dew point of −50° C., 4.2 g of 4,4,4-trifluoro-3-hydroxy-3-(trifluoromethyl)butyric acid (HOC(CF$_3$)$_2$CH$_2$COOH) were dissolved in 20 ml of dimethyl carbonate. Next, 1.3 g of lithium tetrakis(methoxy)borate (LiB(OCH$_3$)$_4$) were slowly added to this solution. After this addition, the solution was heated to 60° C. and allowed to react for 10 hours. Dimethyl carbonate was removed from the resulting reaction solution under a reduced pressure condition of 120° C. and 1 torr, thereby obtaining 4.3 g of a white solid as a product. This product was identified by NMR spectrum and elementary analysis as being LiB(OC(CF$_3$)$_2$CH$_2$COO)$_2$.

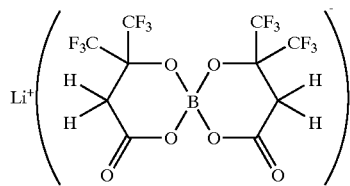

The NMR spectrum of the product is shown below.

$^{19}$F-NMR (hexafluorobenzene standard, solvent: CD$_3$CN) 85.0 ppm (12F, s)

$^1$H-NMR 2.86 ppm (2H, d, J=16 Hz) 2.75 ppm (2H, d, J=16 Hz)

Next, the obtained compound was dissolved in a mixed solution of ethylene carbonate (EC) and dimethyl carbonate (DMC) (EC:DMC=1:1) to prepare an electrolytic solution having an electrolyte concentration of 0.8 mol/dm$^3$ followed by measurement of ion conductivity by the alternating current bipolar-type cell. As a result, the ion conductivity was 1.9 mS/cm.

A charging and discharging test of an actual cell was conducted using the above-mentioned electrolyte. A test cell (half cell) was prepared in the manner described below. 10 parts by weight of polyvinylidene fluoride (PVDF) as a binder were mixed with 90 parts by weight of natural graphite powder followed by the addition of N,N-dimethylformamide to prepare a slurry. This slurry was applied to a nickel mesh and allowed to dry for 12 hours at 150° C. to prepare a test negative electrode. Lithium metal was used for a counter electrode. A glass fiber filter as a separator was impregnated with the above-mentioned electrolytic solution, thereby assembling the half cell.

A constant current charging and discharging test was then conducted under the conditions indicated below. The current density was 0.3 mA/cm$^2$ for both charging and discharging, while charging was performed until 0.0 V and discharging until 1.5 V (vs. Li/Li$^+$). As a result, the initial discharge capacity was 320 mAh/g. Although charging and discharging were repeated 20 times, results were obtained in which the capacity of the 20$^{th}$ cycle was 97% of the initial capacity.

Comparative Example 1

LiPF$_6$ was dissolved in a mixed solvent of ethylene carbonate (EC) and dimethyl carbonate (DMC) (EC:DMC=1:1) to prepare an electrolytic solution having an electrolyte concentration of 1 mol/dm$^3$. Next, this electrolytic solution was placed in a fluororesin container, and, when subjected to a heat resistance test by storing for 1 month at 100° C., the electrolytic solution changed to have a yellow color.

When water was added to this electrolytic solution prior to conducting the heat resistance test, various hydrolysis products were found by NMR. Substances detected as hydrolysis products included hydrogen fluoride and phosphorus oxychloride.

Comparative Example 2

LiN(CF$_3$SO$_2$)$_2$ was dissolved in a mixed solvent of ethylene carbonate (EC) and dimethyl carbonate (DMC) (EC:DMC=1:1) to prepare an electrolytic solution having an electrolyte concentration of 1 mol/dm$^3$. Next, a corrosion test of an aluminum separator was conducted using this electrolyte. A beaker type cell was used for the test cell, using aluminum for the working electrode, and lithium metal for the counter electrode and reference electrode. When the working electrode was held at 5 V (Li/Li$^+$), current flowed and the current value increased with time. Following testing, when the surface of the working electrode was observed by SEM, severe corrosion pits were found in the aluminum surface.

What is claimed is:

1. An electrolyte for an electrochemical device, said electrolyte comprising an ionic metal complex represented by the general formula (1):

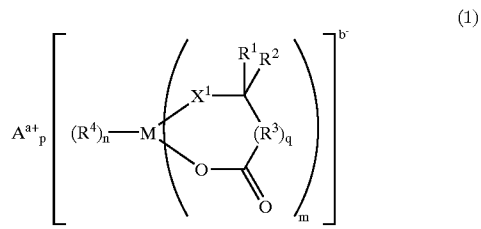

wherein M is a transition metal selected from the group consisting of Sc, Ti, V, Cr, Mn, Cu, Y, Zr, Nb, Mo, Tc, Ag, La, Ce, Pr, Nd, Pm, Sm, Eu, Gd, Tb, Dy, Ho, Er, Tm, Yb, Lu, Hf, Ta, W, Re, Au, Ac, Th, Pa, U, Np, Pu, Am, Cm, Bk, Cf, Es, Fm, Md, No, and Lr, or an element selected from the group consisting of elements of groups 12–15 of the periodic table; A$^{a+}$ represents a metal ion, onium ion or proton; provided that M is not B when A$^{a+}$ is Cs$^+$; a represents a number from 1 to 3; b represents a number from 1 to 3; p is b/a; m represents a number from 1 to 3; n represents a number from 0 to 4; q is 0 or 1; X$^1$ represents O, S or NR$^5$R$^6$; each of R$^1$ and R$^2$ independently represents H, a halogen, a C$_1$–C$_{10}$ alkyl group or C$_1$–C$_{10}$ halogenated alkyl group; R$^3$ represents a C$_1$–C$_{10}$ alkylene group, C$_1$–C$_{10}$ halogenated alkylene group, C$_4$–C$_{20}$ aryl group or C$_4$–C$_{20}$ halogenated aryl group; R$^4$ represents a halogen, C$_1$–C$_{10}$ alkyl group, C$_1$–C$_{10}$ halogenated alkyl group, C$_4$–C$_{20}$ aryl group, C$_4$–C$_{20}$ halogenated aryl group or X$^2$R$^7$; X$^2$ represents O, S or NR$^5$R$^6$; each of R$^5$ and R$^6$ represents H or a C$_1$–C$_{10}$, alkyl group; and R$^7$ represents a C$_1$–C$_{10}$ alkyl group, C$_1$–C$_{10}$ halogenated alkyl group, C$_4$–C$_{20}$ aryl group or C$_4$–C$_{20}$ halogenated aryl group.

2. An electrolyte according to claim 1, wherein said M is an element selected from the group consisting of Al, B, V, Ti, Si, Zr, Ge, Sn, Cu, Y, Zn, Ga, Nb, Ta, Bi, P, As, Sc, Hf, and Sb.

3. An electrolyte according to claim 2, wherein said M is an element selected from the group consisting of Al, B and P.

4. An electrolyte according to claim 1, wherein said A$^{a+}$ is a lithium ion, quaternary ammonium ion or proton.

5. An electrolyte according to claim 1, wherein at least one of said R$^1$ and said R$^2$ is a fluorinated alkyl group.

6. An electrolyte according to claim 5, wherein said fluorinated alkyl group is trifluoromethyl group.

7. An electrolyte according to claim 1, wherein R$^3$ is such that a chelate ring containing said M in the general formula (1) is a closed loop of bonded atoms of 5–10 in number.

8. An electrolyte according to claim 1, wherein said R$^7$ is a C$_1$–C$_{10}$ fluorinated alkyl group.

9. An ion conductor for an electrochemical device, said ion conductor comprising:

an electrolyte according to claim 1; and a member selected from the group consisting of a nonaqueous solvent, a polymer and a mixture thereof, said member dissolving therein said electrolyte.

10. An ion conductor according to claim 9, wherein said nonaqueous solvent is an aprotic solvent.

11. An ion conductor according to claim 9, wherein said polymer is an aprotic polymer.

12. An ion conductor according to claim 9, which has a concentration of said electrolyte within a range of from 0.1 mol/dm$^3$ to a saturated concentration.

13. An ion conductor according to claim 12, wherein said concentration is within a range of from 0.5 mol/dm$^3$ to 1.5 mol/dm$^3$.

14. An electrochemical device comprising:

(a) an ion conductor; and (b) first and second electrodes received in said ion conductor;

wherein said ion conductor comprises:

(1) an electrolyte according to claim 1; and (2) a further constituent selected from the group consisting of a nonaqueous solvent, a polymer and a mixture thereof, wherein said electrolyte is dissolved in said further constituent.

15. An electrochemical device according to claim 14, wherein said electrochemical device is a lithium cell or a lithium ion cell.

16. An electrolyte for an electrochemical device, said electrolyte comprising an ionic metal complex represented by the general formula (1):

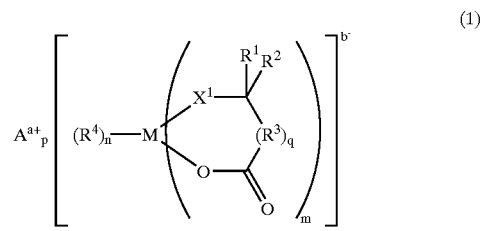

wherein M is a transition metal selected from the group consisting of elements of groups 3–11 of the periodic table or an element selected from the group consisting of elements of groups 12–15 of the periodic table; $A^{a+}$ represents a metal ion, onium ion or proton; a represents a number from 1 to 3; b represents a number from 1 to 3; p is b/a; m represents a number from 1 to 3; n represents a number from 0 to 4; q is 0 or 1; $X^1$ represents O, S or $NR^5R^6$; each of $R^1$ and $R^2$ independently represents a $C_1$–$C_{10}$ halogenated alkyl group; $R^3$ represents a $C_1$–$C_{10}$ akylene group, $C_1$–$C_{10}$ halogenated alkylene group, $C_4$–$C_{20}$ aryl group or $C_4$–$C_{20}$ halogenated aryl group; $R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$; $X^2$ represents O, S or $NR^5R^6$; each of $R^5$ and $R^6$ represents H or a $C_1$–$C_{10}$, alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group.

* * * * *